United States Patent
Donovan et al.

(10) Patent No.: US 8,617,053 B2
(45) Date of Patent: Dec. 31, 2013

(54) REMOTE POSITION CONTROL FOR SURGICAL APPARATUS

(75) Inventors: Brian W. Donovan, San Jose, CA (US); Bryan A. Click, Fremont, CA (US)

(73) Assignee: Warsaw Othropedic, Inc., Warsaw, IN (US)

( * ) Notice: Subject to any disclaimer, the term of this patent is extended or adjusted under 35 U.S.C. 154(b) by 952 days.

(21) Appl. No.: 12/430,044

(22) Filed: Apr. 24, 2009

(65) Prior Publication Data

US 2010/0274080 A1  Oct. 28, 2010

(51) Int. Cl.
*A61B 1/00* (2006.01)
*A61B 17/58* (2006.01)
*A61M 29/00* (2006.01)
*A61F 2/28* (2006.01)

(52) U.S. Cl.
USPC ............. 600/104; 606/93; 606/191; 606/192; 623/23.47; 623/23.48

(58) Field of Classification Search
USPC ........... 606/62, 63, 86, 92–94, 104–107, 192; 623/23.47–23.48; 600/104; 604/117, 604/136–139, 200–207, 218, 224, 232, 264
See application file for complete search history.

(56) References Cited

U.S. PATENT DOCUMENTS

| | | | |
|---|---|---|---|
| 5,350,355 A * | 9/1994 | Sklar | 604/23 |
| 6,719,773 B1 * | 4/2004 | Boucher et al. | 606/192 |
| 7,297,136 B2 | 11/2007 | Wyrick | |
| 2001/0047151 A1 | 11/2001 | Xian et al. | |
| 2005/0113843 A1 * | 5/2005 | Arramon | 606/94 |
| 2005/0234461 A1 | 10/2005 | Burdulis, Jr. et al. | |
| 2006/0122621 A1 | 6/2006 | Truckai et al. | |
| 2008/0021463 A1 | 1/2008 | Georgy | |

* cited by examiner

*Primary Examiner* — David Isabella
*Assistant Examiner* — Yashita Sharma

(57) ABSTRACT

A system for performing a minimally invasive surgical procedure includes a cannula, a surgical instrument for use through the cannula, and a remote positioning system to adjust the relative position between the surgical instrument and the cannula. By allowing a physician to perform the minimally invasive surgical procedure at a distance from the patient, the remote positioning system minimizes the radiation exposure of the physician while still providing accurate control over the procedure.

20 Claims, 13 Drawing Sheets

REMOTE POSITION CONTROL FOR SURGICAL APPARATUS

FIELD OF THE INVENTION

The invention relates to a system and method for performing a surgical procedure, and in particular, to a medical kit or system that includes a depth control mechanism that can be operated remotely.

BACKGROUND OF THE INVENTION

A minimally invasive procedure (sometimes referred to as a percutaneous procedure) is a medical procedure that is performed through the skin or an anatomical opening. In contrast to an open procedure for the same purpose, a minimally invasive procedure will generally be less traumatic to the patient and result in a reduced recovery period.

For example, for many individuals in our aging world population, undiagnosed and/or untreatable bone strength losses have weakened these individuals' bones to a point that even normal daily activities pose a significant threat of fracture. In one common scenario, when the bones of the spine are sufficiently weakened, the compressive forces in the spine can cause fracture and/or deformation of the vertebral bodies. For sufficiently weakened bone, even normal daily activities like walking down steps or carrying groceries can cause a collapse of one or more spinal bones. A fracture of the vertebral body in this manner is typically referred to as a vertebral compression fracture. Other commonly occurring fractures resulting from weakened bones can include hip, wrist, knee and ankle fractures, to name a few.

Fractures such as vertebral compression fractures often result in episodes of pain that are chronic and intense. Aside from the pain caused by the fracture itself, the involvement of the spinal column can result in pinched and/or damaged nerves, causing paralysis, loss of function, and intense pain which radiates throughout the patient's body. Even where nerves are not affected, however, the intense pain associated with all types of fractures is debilitating, resulting in a great deal of stress, impaired mobility and other long-term consequences. For example, progressive spinal fractures can, over time, cause serious deformation of the spine ("kyphosis"), giving an individual a hunched-back appearance, and can also result in significantly reduced lung capacity and increased mortality.

Until recently, treatment options for vertebral compression fractures, as well as other serious fractures and/or losses in bone strength, were extremely limited—mainly pain management with strong oral or intravenous medications, reduced activity, bracing and/or radiation therapy, all with mediocre results. Because patients with these problems are typically older, and often suffer from various other significant health complications, many of these individuals are unable to tolerate invasive surgery. In addition, to curb further loss of bone strength, many patients are given hormones and/or vitamin/mineral supplements—again with mediocre results and often with significant side effects.

In an effort to more effectively and directly treat vertebral compression fractures, minimally invasive techniques such as vertebroplasty and, subsequently, kyphoplasty, have been developed. Vertebroplasty involves the injection of a flowable bone filler material, usually polymethylmethacrylate (PMMA—commonly known as bone cement), into a fractured, weakened, or diseased vertebral body. Shortly after injection, the liquid filling material hardens or polymerizes, desirably supporting the vertebral body internally, alleviating pain and preventing further collapse of the injected vertebral body.

Because the liquid bone cement naturally follows the path of least resistance within bone, and because the small-diameter needles used to deliver bone cement in vertebroplasty procedure require either high delivery pressures and/or less viscous bone cements, ensuring that the bone cement remains within the already compromised vertebral body is a significant concern in vertebroplasty procedures. Kyphoplasty addresses this issue by first creating a cavity within the vertebral body (e.g., with an inflatable balloon) and then filling that cavity with bone filler material. The cavity provides a natural containment region that minimizes the risk of bone filler material escape from the vertebral body. An additional benefit of kyphoplasty is that the creation of the cavity can also restore the original height of the vertebral body, further enhancing the benefit of the procedure.

In both vertebroplasty and kyphoplasty, as with most minimally invasive procedures, x-ray fluoroscopy is used to allow the surgeon to visualize the procedural actions being performed within the patient. Unfortunately, due to the constrained access requirements of minimally invasive procedures, tools associated with such procedures have typically been designed to be manipulated in close proximity to the actual access location to the patient's body. Therefore, the surgeon performing a minimally invasive procedure can be exposed to the radiation field from the fluoroscopy system. For a surgeon performing a large number of procedures, the cumulative radiation exposure from those procedures can be significant.

Accordingly, it is desirable to provide surgical tools and techniques that minimize the radiation exposure to a surgeon.

SUMMARY OF THE INVENTION

By incorporating remotely activated position control capabilities, a minimally invasive surgical system can be used to effectively perform a minimally invasive surgical procedure while allowing the surgeon to remain outside the radiation field.

In one embodiment, a system for performing a minimally invasive surgical procedure can include a cannula, a surgical instrument (e.g., an inflatable bone tamp, a mechanical cavity creation device, a bone filler material delivery nozzle, etc.) sized to fit through the cannula, and a positioning system for controlling the relative positioning of the surgical instrument with respect to the cannula. The positioning system can include a positioning mechanism that can be coupled to the cannula and surgical instrument, and a remote position controller for controlling the positioning mechanism.

In various embodiments, the system can further include an actuation system for the surgical instrument (e.g., an inflation syringe for an inflatable bone tamp, a remote actuator for a mechanical cavity creation device, a hydraulic pump to cause bone filler material to be delivered via the nozzle, etc.). In various other embodiments, the system can further include additional tools (e.g., introducer needles, guide wires, obturators, drills, etc.) for use in performing the minimally invasive surgical procedure. In various other embodiments, the system can further include instructions for use describing the use of the system.

In various embodiments, the positioning mechanism can include a fixed element that can be coupled to the cannula and an articulating element that can be coupled to the surgical instrument, with the articulating element being coupled to the fixed element by a hinge, a linkage, a living hinge, an elastic element, a linear actuator, a linear guide, a bearing, a lead screw, a hydraulic or pneumatic cylinder, or any other mechanism that enables relative motion between the articulating element and the fixed element. The remote position controller can communicate with positioning mechanism via a communication path (e.g., a cable, rod, linkage, wire (for physical input), wire (for analog or digital input), fiber, wireless link, or any other path for conveying input at remote position controller to positioning mechanism).

In various embodiments, the communication path can be a jacketed cable (e.g., a push-pull cable) that includes an outer jacket having a distal end coupled to the fixed element and an inner cable having a distal end coupled to the articulating element (or vice versa). By moving the inner cable relative to the outer jacket, the relative position of the articulating element (and hence the surgical instrument) can be adjusted relative to the fixed element (and hence the cannula). This positioning can be continuously variable, or can have discrete positional stops to define specific positioning configurations for the surgical instrument and the cannula. In various embodiments, the remote position controller can include a lever, dial/spool, or threaded element for moving the inner cable relative to the outer jacket.

In various other embodiments, the positioning mechanism can further include a biasing element or mechanism (e.g., a spring or other resilient element) that biases the articulating element towards a default position relative to the cannula. In some embodiments, this biasing element can cause the surgical instrument to be fully retracted into the cannula when a specific extension signal is not being provided by the remote position controller.

In various other embodiments, the surgical instrument can be a nozzle for delivering bone filler material, and the system can further include a hydraulic pump to drive the bone filler material through the nozzle, and a second hydraulic line from the hydraulic pump can be used to provide the control signal to the positioning mechanism. The common hydraulic pressure can then be used to retract the nozzle towards the cannula as the bone filler material is dispensed from the nozzle, thereby allowing the nozzle to remain clear of the deposited bone filler material.

In another embodiment, a method for performing a minimally invasive surgical procedure can include placing a cannula in a patient to define an access path to a target surgical location, providing a surgical instrument in the cannula, providing a position control mechanism coupled to the cannula and to the surgical instrument, and remotely controlling the position control mechanism to adjust the position of the surgical instrument relative to the cannula.

In one embodiment, remotely controlling the positioning mechanism can be accomplished by moving the proximal end of inner cable relative to a jacket surrounding the inner cable, with the distal end of the inner cable being coupled to an articulating element in the positioning mechanism coupled to the surgical instrument, and the distal end of the jacket being coupled to a fixed element of the positioning mechanism coupled to the cannula.

In other embodiments of the method for performing the minimally invasive surgical procedure, the surgical instrument can be a nozzle for delivering bone filling material to the target surgical location, and adjusting the position of the surgical instrument relative to the cannula can include retracting the nozzle towards the cannula as it dispenses the bone filling material, or moving the nozzle to a location in the target surgical location (e.g., in the center of a cavity formed within the cancellous bone of a vertebra) and maintaining that position as the nozzle dispenses the bone filler material.

In another embodiment, a nozzle for delivering bone filler material to a target surgical location can include a valve at a distal tip of the nozzle to selectively close off the nozzle opening. In one embodiment, the valve can include a stopper sized to cover the opening at the distal tip of the nozzle, and a cable or rod running through the nozzle to pull the stopper against the distal tip of the nozzle. In one embodiment, the cable/rod can be spring loaded to pull the stopper against the distal tip of the nozzle (i.e., a normally closed valve).

As will be realized by those of skilled in the art, many different embodiments of an introducer/guide pin device, systems, kits, and/or methods of using an introducer/guide pin device according to the present invention are possible. Additional uses, advantages, and features of the invention are set forth in the illustrative embodiments discussed in the detailed description herein and will become more apparent to those skilled in the art upon examination of the following.

DETAILED DESCRIPTION

By incorporating remotely activated position control capabilities, a minimally invasive surgical system can be used to effectively perform a minimally invasive surgical procedure while allowing the surgeon to remain outside the radiation field.

Figure 1:
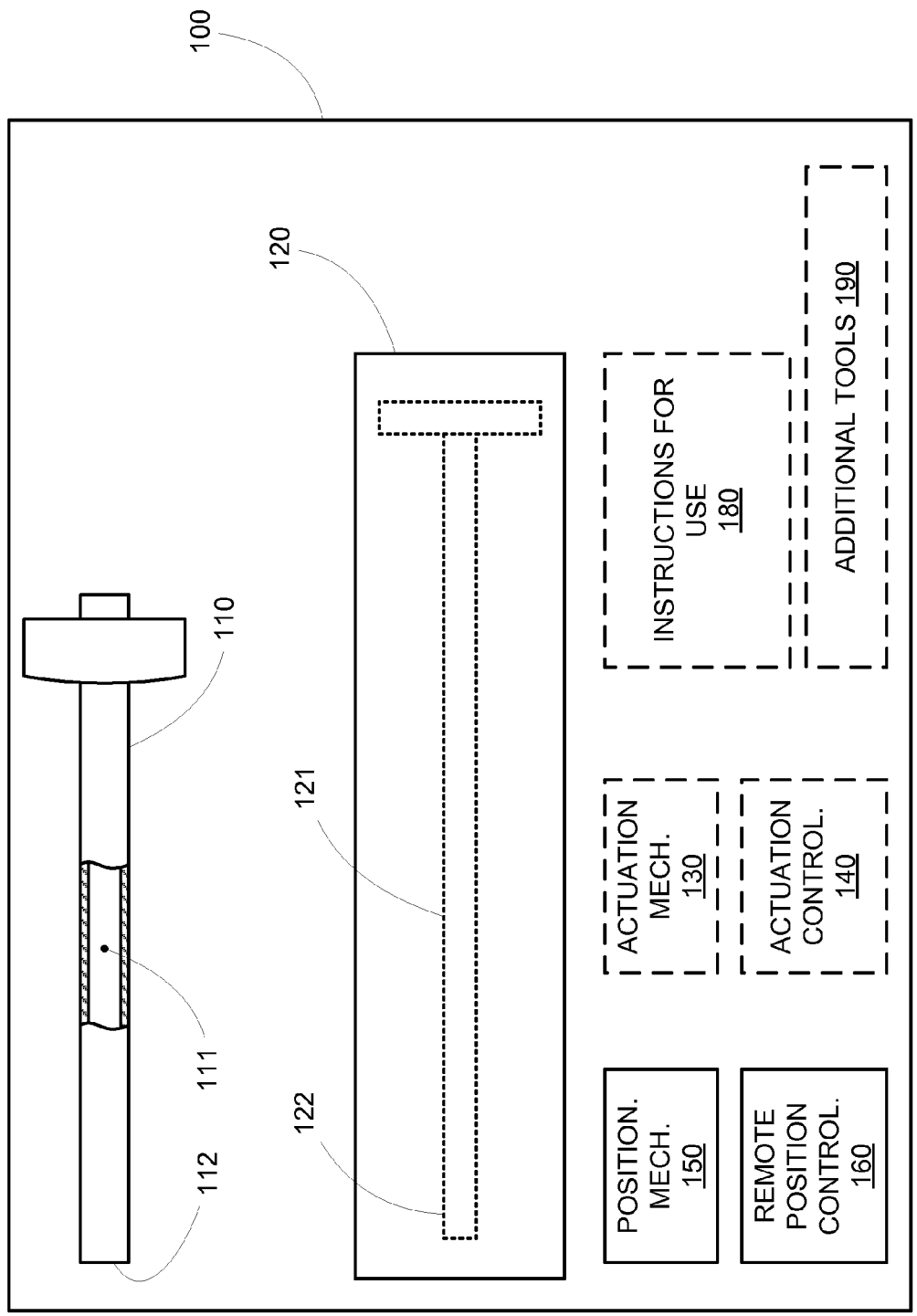
FIG. 1 depicts a system that includes a cannula, a surgical instrument for performing a percutaneous surgical procedure, and a remote positioning system for controlling the placement of the surgical instrument relative to the cannula.

FIG. 1 shows a system 100 of functional instruments that can be used to perform a minimally invasive surgical procedure. In various embodiments, system 100 can comprise a kit providing a prepackaged set of instruments for performing the surgical procedure.

System 100 includes a cannula 110 and a surgical instrument 120 that is sized to perform a percutaneous procedure through a lumen 111 of cannula 110. System 100 further includes a positioning mechanism 150 that can be coupled to cannula 110 and surgical instrument 120, and a remote position controller 160 that directs positioning mechanism 150 to adjust the position of surgical instrument 120 relative to cannula 110. Note that according to various embodiments of the invention, positioning mechanism 150, remote position controller 160, cannula 110, and surgical instrument 120 can be part of a single kit, or can be grouped in any combination of elements (e.g., cannula 110 and surgical instrument 120 packaged together, with positioning mechanism 150 and remote position controller 160 packaged separately).

In various embodiments, remote position controller 160 can control positioning mechanism 150 via direct physical manipulation (e.g., using a cable, wire, linkage, tube, or any other mechanical (including hydraulic) connection), via non-physical control signals (e.g., electrical, optical, magnetic, or other signals transmitted either over a physical path such as a wire or fiber, or wirelessly), or a combination of the two. By enabling remote position control of surgical instrument 120, positioning mechanism 150 and remote position controller 160 beneficially allow a percutaneous procedure to be performed by a physician outside of the radiation field used for procedure visualization.

Note that as used herein, "remotely controlling" or "remote control" refers to controlling inputs being applied at some distance from the object being controlled. For example, grasping a surgical instrument by hand and moving it within a cannula is not "remote control", but a long cable or rod coupled to the surgical instrument and/or cannula that can adjust the relative position of the two does provide "remote control". Preferably, such remote control is provided via a flexible signal path (e.g., a flexible cable or wire or wireless link), to allow the physician maximum freedom of motion during use.

In various other embodiments, system 100 can further include an optional actuation mechanism 130 for deploying or activating surgical instrument 120, and an optional remote actuation controller 140 to enable remote control over surgical instrument 120. Just as remote position controller 160 enables positioning of surgical instrument 120 from outside the procedure radiation field, remote actuation controller 140 and/or actuation mechanism 130 can allow the physician to perform the procedure while remaining outside the radiation field.

In one embodiment, surgical instrument 120 can be a device for creating a cavity in cancellous bone during a kyphoplasty or other bone-reinforcing procedure. For example, surgical instrument 120 could be an inflatable bone tamp, mechanical void creation device (e.g., expandable structure, cutting element(s), etc.), or a device for creating a cavity in bone by any other means (e.g., heat, ultrasound, radio frequency energy, etc.). Positioning mechanism 150 could attach to surgical instrument 120 and cannula 110, and the extension of the distal end 122 of surgical instrument 120 beyond the distal tip 112 of cannula 110 could be controlled by remote position control 160. In this manner, system 100 could enable targeted cavity formation within cancellous bone by remote positioning and/or movement of surgical instrument 120.

For example, if surgical instrument 120 is a inflatable bone tamp (e.g., a balloon catheter with an inflatable balloon configured to compress cancellous bone and apply a lifting force to the endplates of a vertebral body), actuation mechanism 130 could be an inflation syringe with a length of tubing or other fluid conveyance channel in fluid communication with the inflatable bone tamp, and actuation control 140 could be a handle, knob, or trigger on the inflation syringe to cause inflation fluid (e.g., air or saline solution) to be expressed from the syringe. The inflation fluid would then be carried by the tubing into the inflatable bone tamp to inflate the inflatable bone tamp and form a cavity in cancellous bone. In this arrangement, surgical instrument (inflatable bone tamp) 120 could be positioned by remote position controller 160, and actuated (inflated/deflated) by actuation controller 140, all from outside the fluoroscopic visualization field, thereby minimizing the radiation exposure for the physician.

Similarly, if surgical instrument 120 is a non-balloon void creation device (i.e., mechanical structure or energy delivery), actuation mechanism 130 could be a deployment, triggering, release, or other mechanism/circuit for deploying/ activating the void creation device, activated by actuation controller 140. Instead of tubing or the like as described with respect to the previous example, in this case the actuation control signals could be conveyed via wire (electrical), mechanical cable, linkage, wireless protocol, or any other means that would allow the physician to remotely control the operation of surgical instrument 120. In this manner, the physician would once again be able to position (relative to cannula 110) and actuate surgical instrument 120 (via remote position controller 160 and actuation controller 140, respectively) from outside the fluoroscopic radiation field.

In another embodiment, surgical instrument 120 could be a device for delivering bone filler material to the interior of a vertebral body (e.g., for a vertebroplasty or kyphoplasty procedure) or any other bone (e.g., for treating a long bone or calcaneus fracture). Surgical instrument 120 could be a delivery nozzle/needle that gains access to the vertebral body through cannula 110, and is positioned relative to cannula 110 by positioning mechanism 150 and remote position controller 160. The bone filler material could then be dispensed from the nozzle/needle at the desired location within the vertebral body by actuation mechanism 130 (e.g., a plunger) in response to actuation controller 140 (e.g., a trigger, knob, hydraulic pump, linkage, or any other system for controlling actuation mechanism 130. Note that the above-described embodiments are exemplary, and any number of other surgical instruments usable with a remote depth control system will be readily apparent.

Note further that system 100 can include any number of additional tools 190, such as introducer needles/guide wires, drills, obturators, handles, among others. System 100 can also include optional instructions for use 180 that describe the proper usage of the tools in system 100 (e.g., as described below with respect to FIG. 3).

Figure 2B:
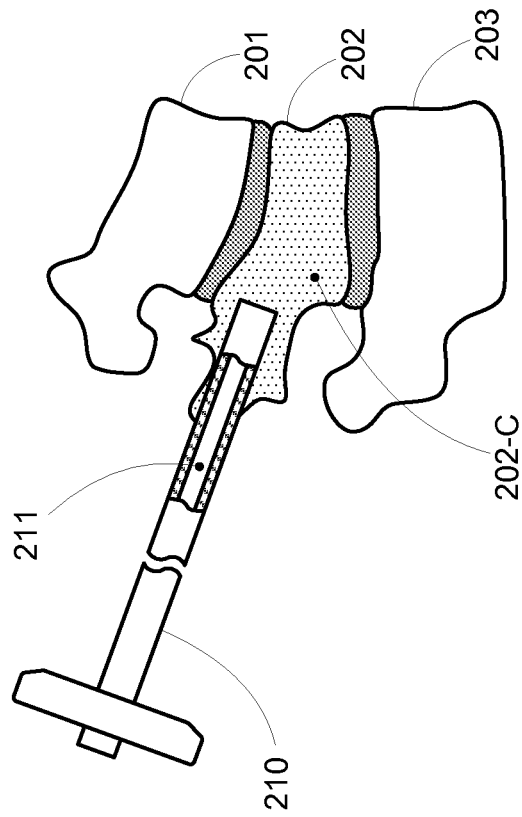
FIGS. 2(A)-2(I) depict a kyphoplasty procedure performed using a remote positioning system that allows the physician performing the procedure to remain outside the fluoroscopic field used to visualize the procedure activity.
Figure 2A:
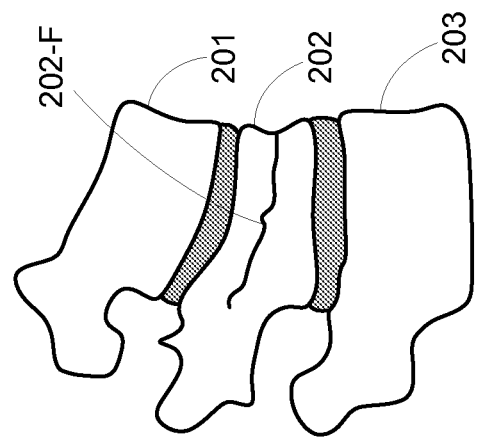

FIGS. 2(A)-2(I) depict an exemplary minimally invasive surgical procedure using a remote positioning system. FIG. 2(A) shows a portion of a human vertebral column, with vertebrae 201, 202, and 203. Vertebra 202 has collapsed due to a vertebral compression fracture (VCF) 202-F that could be the result of osteoporosis or cancer-related weakening of the bone. The abnormal curvature of the spine caused by VCF 202-F can lead to severe pain and further fracturing of adjacent vertebral bodies.

One treatment for this type of fracture is to perform a minimally invasive procedure in which a reinforcing bone filler material is injected into the fractured vertebra, either directly into the fractured region (vertebroplasty) or into a cavity created beforehand in the cancellous bone structure (kyphoplasty). Kyphoplasty is often a preferred technique due to the potential height restoration that can be achieved during the cavity creation phase of the procedure.

FIG. 2(B) shows a cannula 210 being positioned next to the target surgical location, which in this case is the cancellous bone structure within fractured vertebra 202. In this manner, a percutaneous path to vertebra 202 is provided via an interior lumen 211 of cannula 210. Typically, cannula 210 is docked against the exterior wall of the vertebral body (using either a transpedicular or extrapedicular approach) using a guide needle and/or dissector, after which a drill or other access tool (not shown) is used to create a path further into the cancellous bone 202-C of vertebra 202. However, any other method of cannula placement can be used to position cannula 210.

Figure 2C:
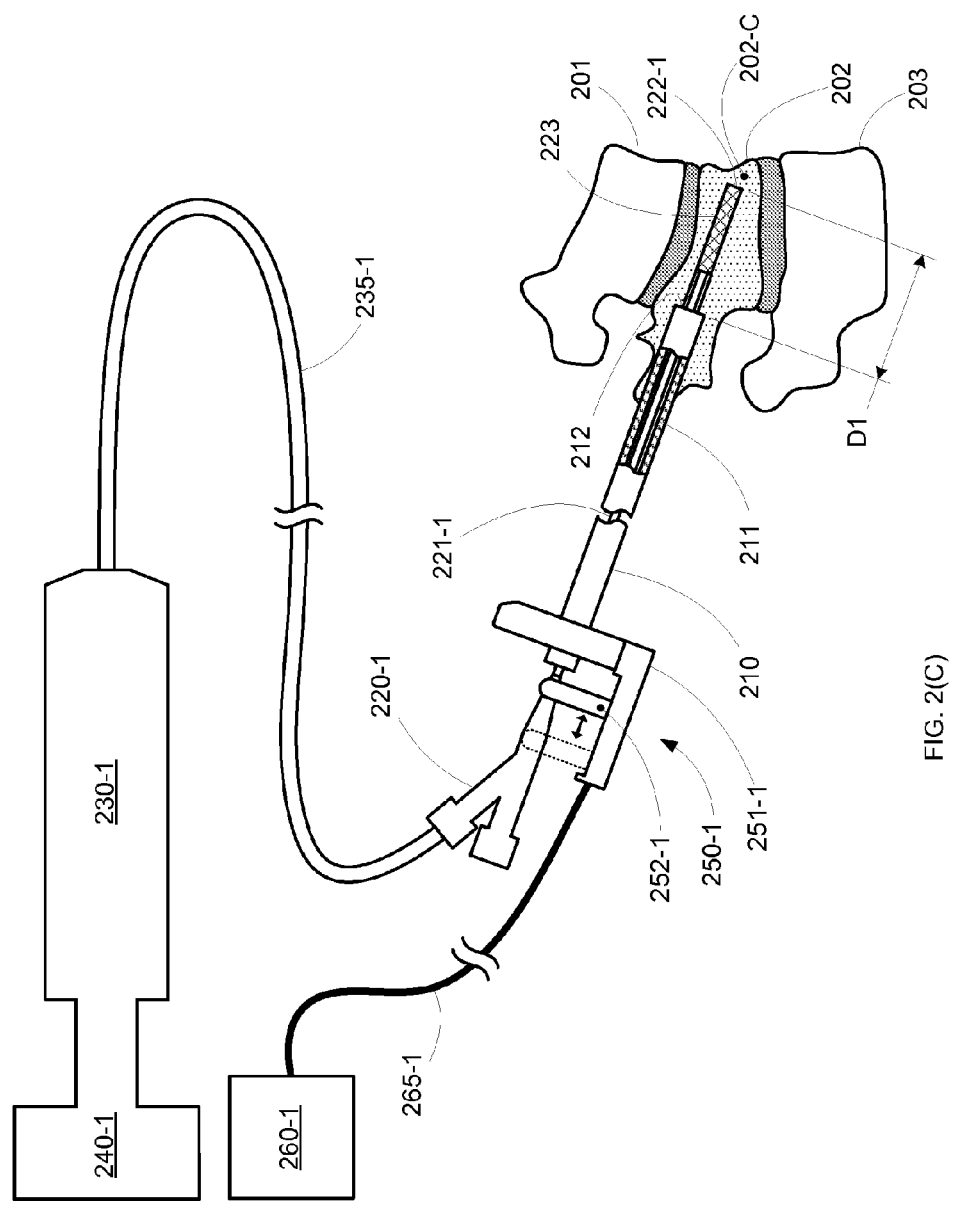

Then in FIG. 2(C), a surgical instrument 220-1 (in this case an inflatable bone tamp) is placed in cannula 220. Inflatable bone tamp 220-1 includes a shaft 221-1 and an expandable structure 223 (e.g., a balloon) at the distal end of shaft 221-1. Inflatable bone tamp 220-1 is coupled to an actuation mechanism 230-1 (in this case an inflation syringe) by a flexible tube 235-1. Inflation syringe 230-1 includes an actuation controller 240-1 (in this case a knob or handle) for causing inflation fluid to be delivered to expandable structure 223 via flexible tube 235-1 and shaft 221-1 of inflatable bone tamp 220-1.

Expandable structure 223, when in an unexpanded state as depicted in FIG. 2(C), is sized to fit within interior lumen 211 of cannula 210, as is shaft 221-1 of inflatable bone tamp 220-1. Therefore, inflatable bone tamp 220-1 can slidably move within lumen 211. A positioning mechanism 250-1 is coupled to cannula 210 and inflatable bone tamp 220-1 to control a distance D1 that inflatable bone tamp 220-1 extends beyond a distal tip 212 of cannula 210 in response to input received at a remote position controller 260-1. In this manner, a physician can use remote position controller 260-1 to adjust the placement of expandable structure 223 within vertebra 202 from a location outside of the fluoroscopic field used to visualize the procedure site.

As noted above with respect to FIG. 1, positioning mechanism 250-1 can be any mechanism/construction that can move inflatable bone tamp 220-1 relative to cannula 210. For instance, positioning mechanism 220-1 can include a fixed element 251-1 coupled to cannula 210, and an articulating element 252-1 coupled to inflatable bone tamp 220-1. In various embodiments, positioning mechanism 220-1 can be coupled to cannula 210 and inflatable bone tamp 220-1 by clips, clamps, snaps, screws, hooks, or any other engaging features and/or fastening device. Note that while articulating element 252-1 is depicted as being coupled to fixed element 251-1 via a sliding interface (e.g., a linear guide or linear actuator), in various other embodiments, articulating element 252-1 can be coupled to fixed element 251-1 by a hinge (including living hinge), lever, linkage, elastic element, pulley system, bearing, solenoid, or any other structure or mechanism that would allow relative movement between the two.

Likewise, remote position controller 260-1 and the control path 265-1 by which it controls positioning mechanism 250-1 can take any form/construction that can provide input from position controller 260-1 to positioning mechanism 250-1. For example, in certain embodiments, control path 265-1 could be a jacketed cable (i.e., a cable capable of transmitting axial loads surrounded by a flexible conduit, such as a push-pull cable) coupled between an adjustment mechanism in remote position controller 260-1 and articulating element 252-1. In other embodiments, control path 265-1 could be a hydraulic line for transmitting a displacement distance at remote position controller 260-1 to articulating element 252-1. In other embodiments, control path 265-1 could be a wired or wireless link for transmitting either analog or digital control signals from remote position controller 260-1 to positioning mechanism 250-1 (e.g., remote position controller 260-1 could provide an "extend" or "retract" signal to a linear actuator in positioning mechanism 250-1 via a wiring harness). Various other embodiments will be readily apparent.

Note also that remote position controller 260-1 and actuation mechanism 230-1/actuation controller 240-1 are shown as being distinct structures for exemplary purposes only. In various other embodiments, position controller 260-1 can be integrated with actuation mechanism 230-1 and/or actuation controller 240-1.

Figure 2D:
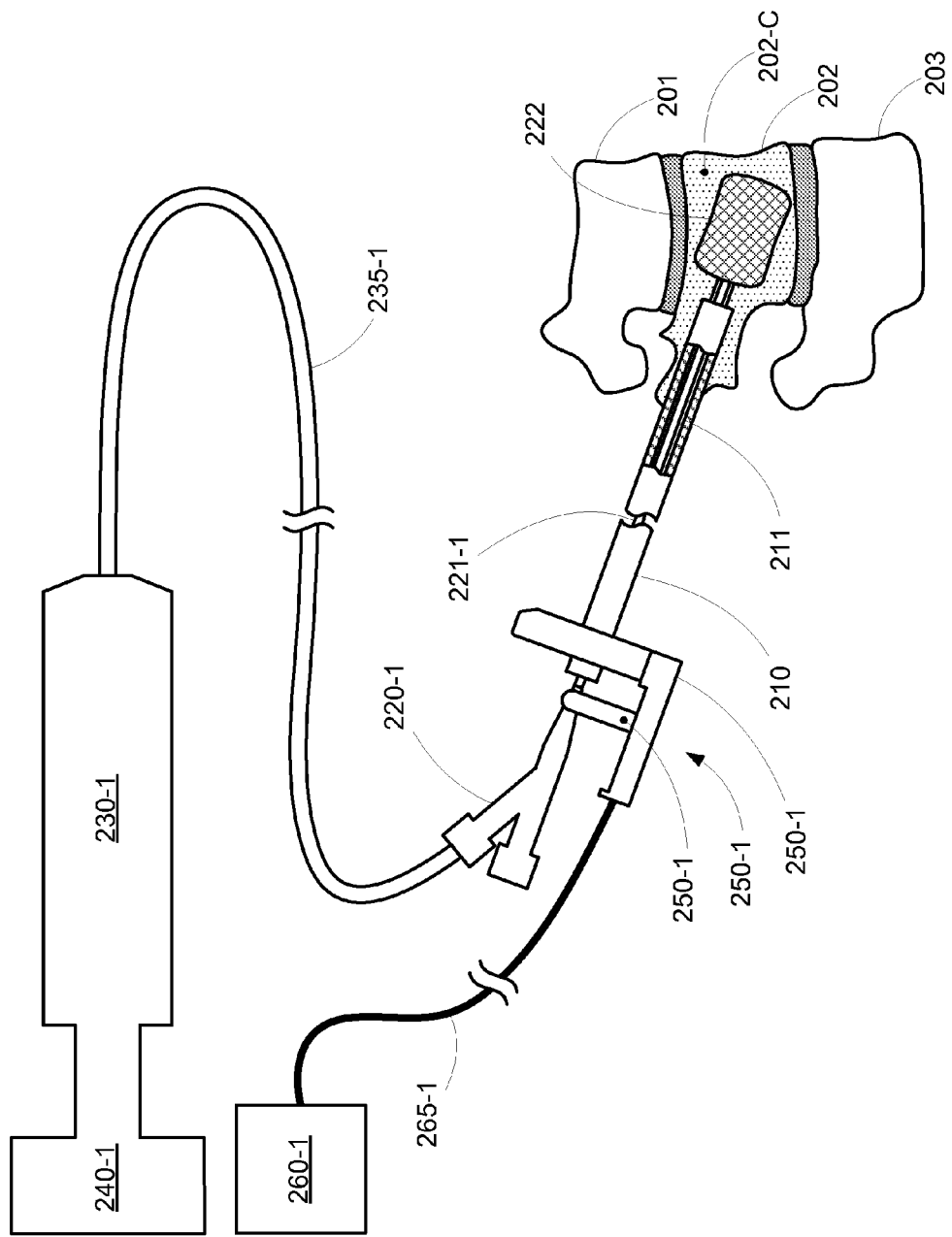
Figure 2E:
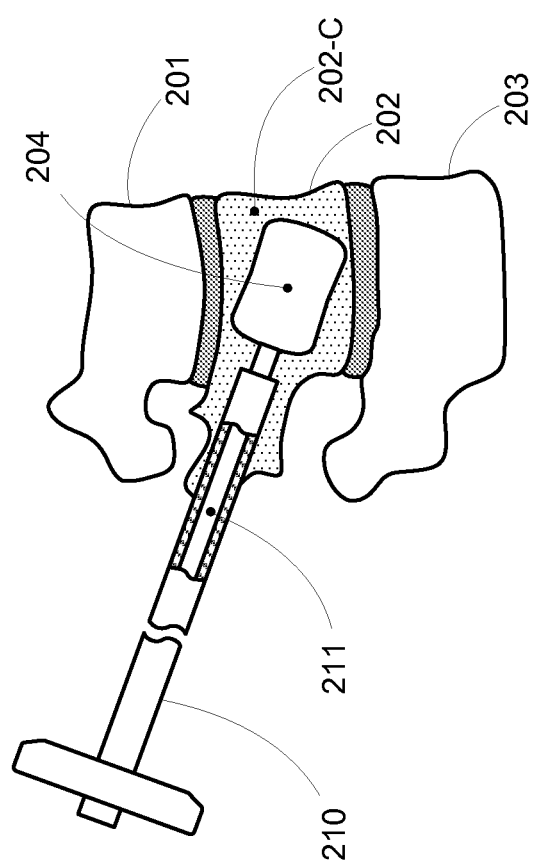

Once expandable structure 223 has been positioned at a desired distance D1 from the tip 212 of cannula 210 by positioning mechanism 250-1 and remote position controller 260-1, handle 240-1 of inflation syringe 230-1 is used to deliver inflation fluid from inflation syringe 230-1, through flexible tube 235-1, and into inflatable bone tamp 220-1, thereby inflating expandable structure 223, as shown in FIG. 2(D). The expansion of expandable structure 222 compresses the surrounding cancellous bone 202-C to create a well-defined cavity within fractured vertebra 202, and can also restore some or all of the original height of the vertebral body.

Note that although the cavity creation process described above is performed by sequentially positioning and then expanding expandable structure 223 for exemplary purposes, in various other embodiments the positioning and expanding operations could be performed multiple times at multiple locations in the vertebral body. In other embodiments, and particularly if structure 223 is a mechanical void creation instrument (e.g., a cutting/compressing element(s) or structure(s), stent, whisk, rasp, osteotome, or coring element, among others) the positioning and expanding operations could be performed simultaneously. In other embodiments, cavity creation in the vertebral body can be performed/supplemented by positioning mechanism 250-1 actually moving the mechanical void creation element within the vertebral body to manipulate the cancellous bone (e.g., scraping, cutting, coring, displacing, etc.).

Upon completion of the above-described operations, inflatable bone tamp 220-1 and the related actuation and positioning accessories can be removed, leaving behind a cavity 204 in the cancellous bone 202-C of vertebra 202. Note that cannula 210 remains docked with vertebra 202 to provide an access path for the subsequent operations described in greater detail below.

Figure 2F:
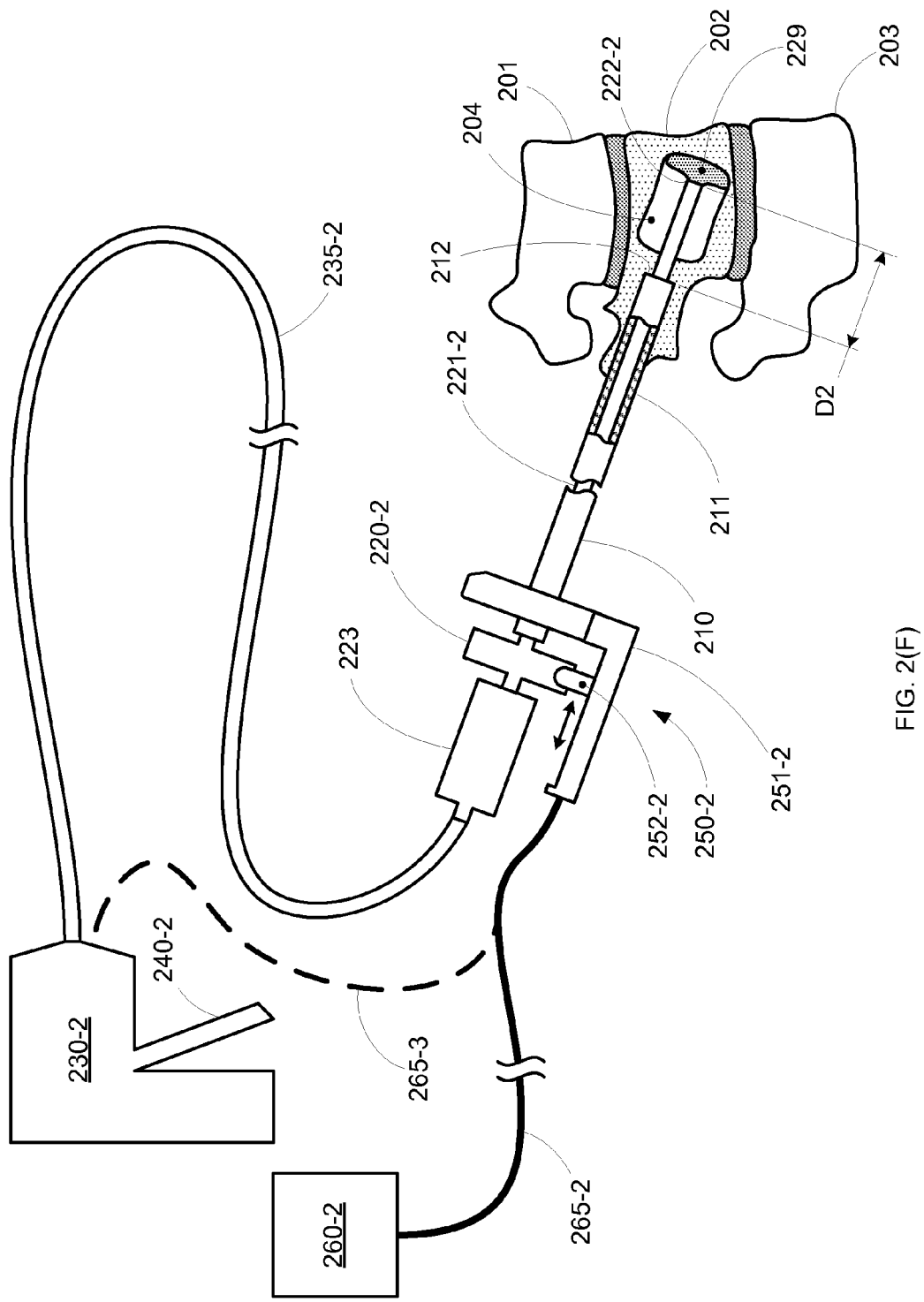

FIG. 2(F) shows a surgical instrument 220-2 (in this case a bone filler material delivery nozzle) placed within cannula 210, with a shaft 221-2 of nozzle 220-2 passing through lumen 211 of cannula 210. A cartridge 223 is attached to nozzle 220-2 to provide a reservoir of bone filler material (e.g., bone cement) for delivery via nozzle 220-2, and is coupled to an actuation mechanism 230-2 (in this case a hydraulic pump) by a hydraulic line 235-2. Hydraulic pump 230-2 includes a trigger 240-2 to increase hydraulic pressure through hydraulic line 235-2 to cause bone filler material 229 to be expressed from cartridge 223 through nozzle 220-2 into cavity 204 of vertebra 202.

Meanwhile, a positioning mechanism 250-2 is coupled to cannula 210 and cement delivery nozzle 220-2 to control a distance D2 that cement delivery nozzle 220-2 extends beyond the distal tip 212 of cannula 210 in response to input from a remote position controller 260-2. Therefore, a physician can use remote position controller 260-2 to adjust the placement of expandable structure 223 within vertebra 202 from a location outside of the fluoroscopic field used to visualize the procedure site.

As noted above with respect to FIG. 2(C), positioning mechanism 250-2 can be any mechanism/construction that can move nozzle 220-2 relative to cannula 210. For instance, positioning mechanism 220-2 can include a fixed element 251-2 coupled to cannula 210, and an articulating element 252-2 coupled to nozzle 220-2. In various embodiments, positioning mechanism 220-2 can be coupled to cannula 210 and cement delivery nozzle 220-2 by clips, clamps, snaps, screws, hooks, or any other engaging features and/or fastening device. Note that while articulating element 252-2 is depicted as being coupled to fixed element 251-2 by a sliding interface (e.g., a linear guide or linear actuator), in various other embodiments, articulating element 252-2 can be coupled to fixed element 251-2 by a hinge (including living hinge), lever, linkage, elastic element, pulley system, bearing, solenoid, or any other structure or mechanism that would allow relative movement between the two.

Likewise, remote position controller 260-2 and the control path 265-2 by which it controls positioning mechanism 250-2 can take any form/construction that can provide input from position controller 260-2 to positioning mechanism 250-2. In some embodiments, control path 265-2 could be a jacketed cable (i.e., a cable capable of transmitting axial loads surrounded by a flexible conduit, such as a push-pull cable) coupled between an adjustment mechanism in remote position controller 260-2 and articulating element 252-2. Movement of the inner cable relative to the outer cable at the proximal end of the jacketed cable (i.e., at remote position controller 260-2) is translated to the distal end of the jacketed cable, and then to positioning mechanism 250-2. In other embodiments, control path 265-2 could be a wired or wireless link for transmitting either analog or digital control signals from remote position controller 260-2 to positioning mechanism 250-2 (e.g., remote position controller 260-2 could provide an "extend" or "retract" signal to a linear actuator in positioning mechanism 250-2 via a wiring harness).

Figure 4A:
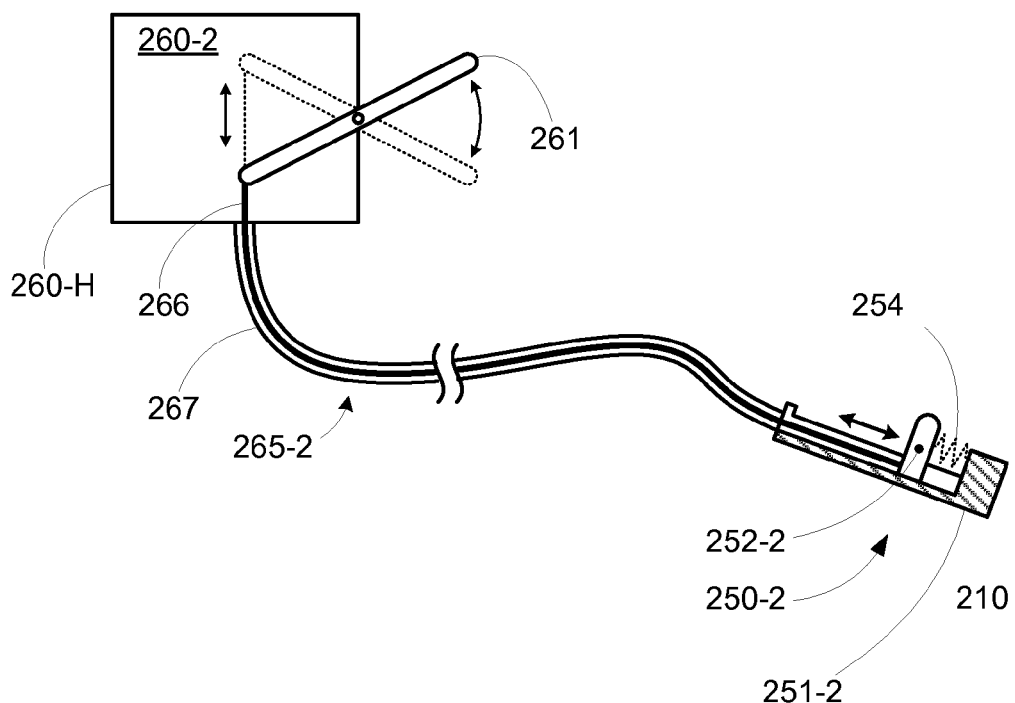
FIGS. 4(A)-4(C) depict various embodiments of remote position controllers.

For example, as shown in FIG. 4(A), control path 265-2 can include a cable 266 within an outer jacket 267 (e.g., a push-pull cable). Outer jacket 267 is connected between a housing 260-H of position controller 260-2 and fixed element 251-2, and cable 266 is connected between articulating element 252-2 and a lever (adjustment mechanism) 261 in position controller 260-2 (lever 261 is movable with respect to housing 260-H). Therefore, moving lever 261 pulls/pushes cable 266 within outer jacket 267 to change the position of articulating element 252-2 relative to fixed element 251-2. Note that in various other embodiments, outer jacket 267 could be connected to articulating element 252-2 and cable 266 could be connected to articulating element 252-2. Lever 261 could be continuously movable, or could have two or more fixed positions, depending on whether continuously variable position control or discrete position settings, respectively, is desired.

In another embodiment, an optional biasing element (e.g., a spring 254) can apply a biasing force to move articulating element 252-2 and fixed element 251-2 towards a default spacing when no force is being applied to lever 261. This in turn defines a default position of the surgical instrument relative to the cannula.

Figure 4B:
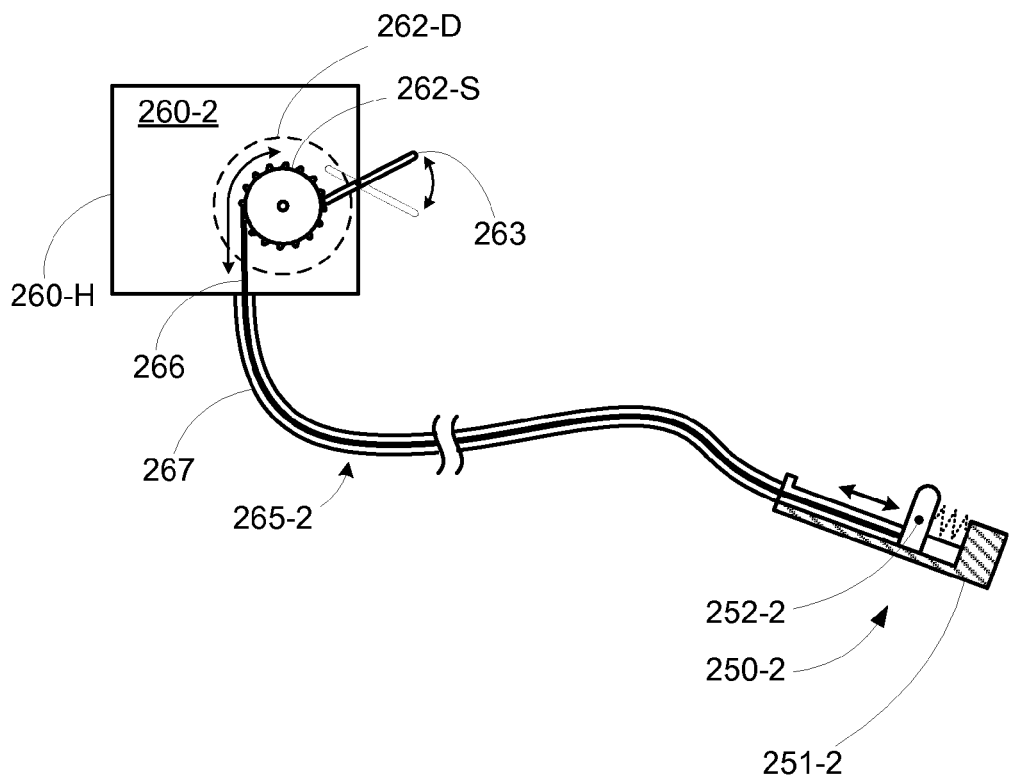

In another embodiment, as shown in FIG. 4(B), lever 261 in FIG. 4(A) can be replaced with a dial (adjustment mechanism) 262-D for winding/unwinding cable 266 around a spool 262-S. This winding/unwinding action then changes the position of articulating element 252-2 relative to fixed element 251-2. An optional biasing element (e.g., a spring 254) can apply a biasing force to move articulating element 252-2 and fixed element 251-2 towards a default spacing when no force is being applied to dial 262-D. In one embodiment, spool 262-S or dial 262-D can include one or more engagement features (e.g., teeth, detents, grooves, ridges, or bumps, among others), and position controller 260-2 can include a latch 263 that can selectively engage the engagement features to lock spool 262-S/dial 262-D in a fixed position at specific positional "stop points". In various other embodiments, dial 262-D could be freely rotatable to provide continuously variable position control.

Figure 4C:
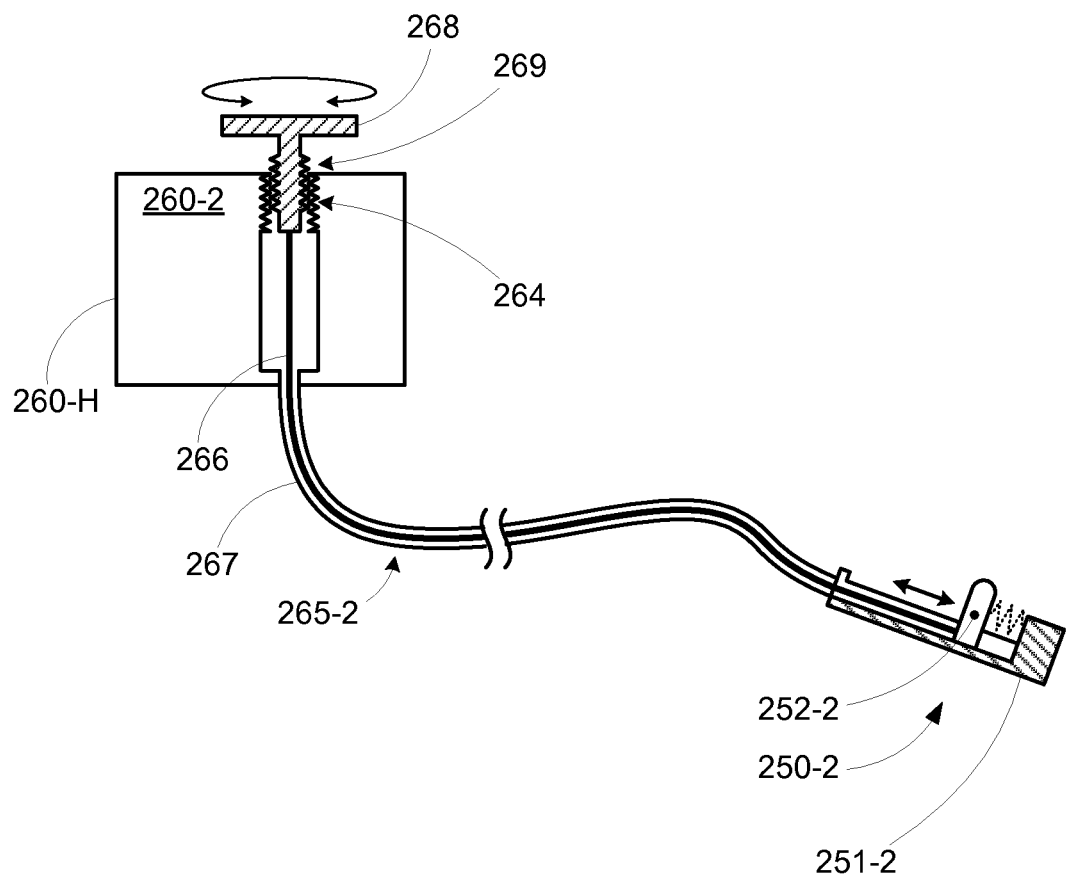

In another embodiment, as shown in FIG. 4(C), lever 261 in FIG. 4(A) or dial 262-S in FIG. 4(B) can be replaced with a threaded element (adjustment mechanism) 268 connected to cable 266. Threads 269 on threaded element 268 mate with threads 264 on housing 260-H of position controller 260-2, so that turning threaded element 268 pulls/pushes cable 266 within outer jacket 267 to change the position of articulating element 252-2 relative to fixed element 251-2. An optional biasing element (e.g., a spring 254) can apply a biasing force to move articulating element 252-2 and fixed element 251-2 towards a default spacing when no force is being applied to threaded element 268 (depending on the frictional resistance between threads 269 and 264). Various other adjustment mechanisms for moving cable 266 relative to outer jacket 267 will be readily apparent.

Returning to FIG. 2(F), in other embodiments, control path 265-2 could be a hydraulic line for transmitting a displacement distance at remote position controller 260-2 to articulating element 252-2. For example, an optional hydraulic line 265-3 could be provided from the same hydraulic pump used to actuate surgical instrument 220-2 (or a different hydraulic pump). In one embodiment, the hydraulic pressure that causes nozzle 220-2 to dispense filler material 229 into cavity 204 can also cause positioning mechanism 250-2 to retract nozzle 220-2 from cavity 204, thereby always keeping nozzle 220-2 out of the mass of dispensed filler material 229. Various other embodiments will be readily apparent.

Figure 2G:
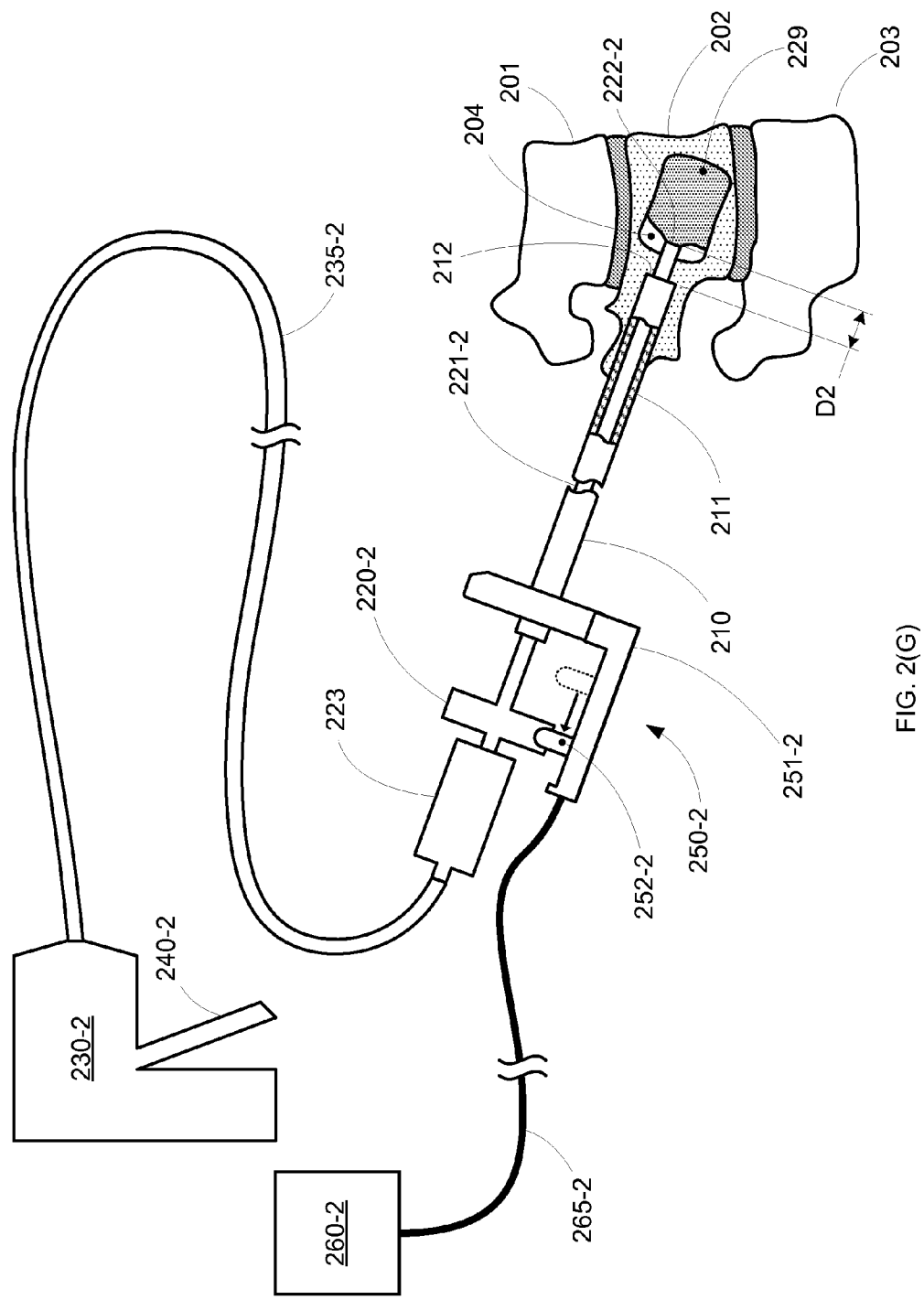

As shown in FIG. 2(G), in one embodiment, remote position controller 260-2 and positioning mechanism 250-2 can draw nozzle 220-2 further into cannula 210 (i.e., decrease distance D2) as actuator 230-2 causes cartridge 223 to dispense filler material 229 into cavity 204 via nozzle 220-2. This can be particularly beneficial when placing bone filler material within longer bones (e.g., when treating fractures of arm or leg bones such as the humerus or femur, respectively, the dispensing nozzle can be retracted as the dispensed bone filler material fills an elongated cavity within the bone, thereby ensuring a consistent fill while minimizing the possibility of the nozzle being cemented into the bone).

Note that in various other embodiments, positioning mechanism 250-2 can be used to place the tip 222-2 of nozzle 220-2 in a specific location (or several discrete locations) as filler material 229 is dispensed. For example, in one embodiment, the tip 222-2 of nozzle 220-2 could be placed in the center of cavity 204 during the entire fill process.

Figure 2H:
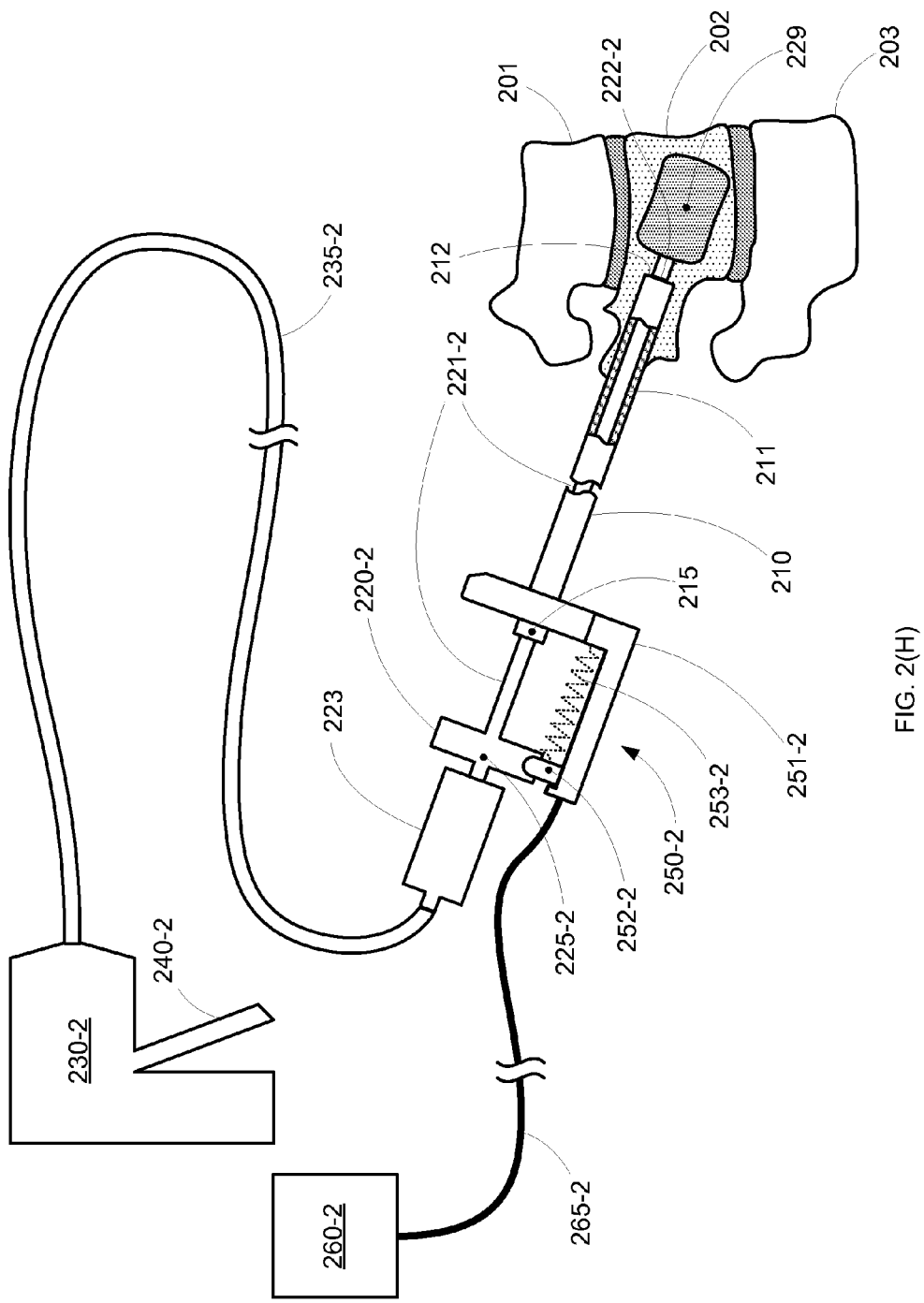

Once filling is complete, nozzle 220-2 can be fully withdrawn into cannula 210, as shown in FIG. 2(H). In some embodiments, positioning mechanism 250-2 can extend/retract nozzle 220-2 one or more times after dispensing is complete to tamp any residual/stray bone filler material 229 into vertebra 202. This tamping operation ensures that no bone filler material remains in cannula 210, and can also minimize the risk of bone filler material being placed anywhere except within vertebra 202.

Note that in some embodiments, it can be desirable to have nozzle 220-2 be withdrawn into cannula 210 as a default configuration. Specifically, in the absence of a specific extension command from remote position controller 260-2, positioning mechanism 250-2 would pull the tip 222-2 of nozzle 220-2 back in to cannula 210. Doing so could prevent nozzle 220-2 from becoming cemented in to vertebral body 202 by the bone filler material 229 (e.g., if the physician inadvertently leaves nozzle 220-2 extended into the mass of deposited bone filler material 229 as it hardens. In one embodiment, this functionality could be provided by a resilient element (e.g., a spring) 253-2 that biases the proximal end 225-2 of surgical instrument 220-2 away from the proximal end 215 of cannula 210. In various other embodiments, remote position controller 260-2 could provide a default control signal to positioning mechanism 250-2 to withdraw nozzle 220-2. Various other embodiments will be readily apparent.

Figure 5A:
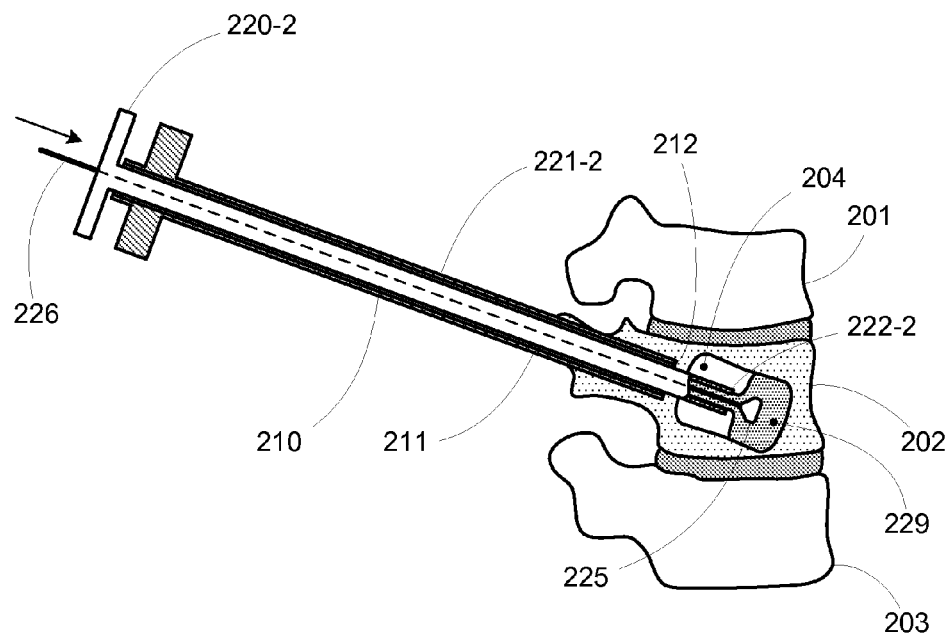
FIGS. 5(A)-5(B) depict an embodiment of a dispensing tip valve for a delivery nozzle.
Figure 5B:
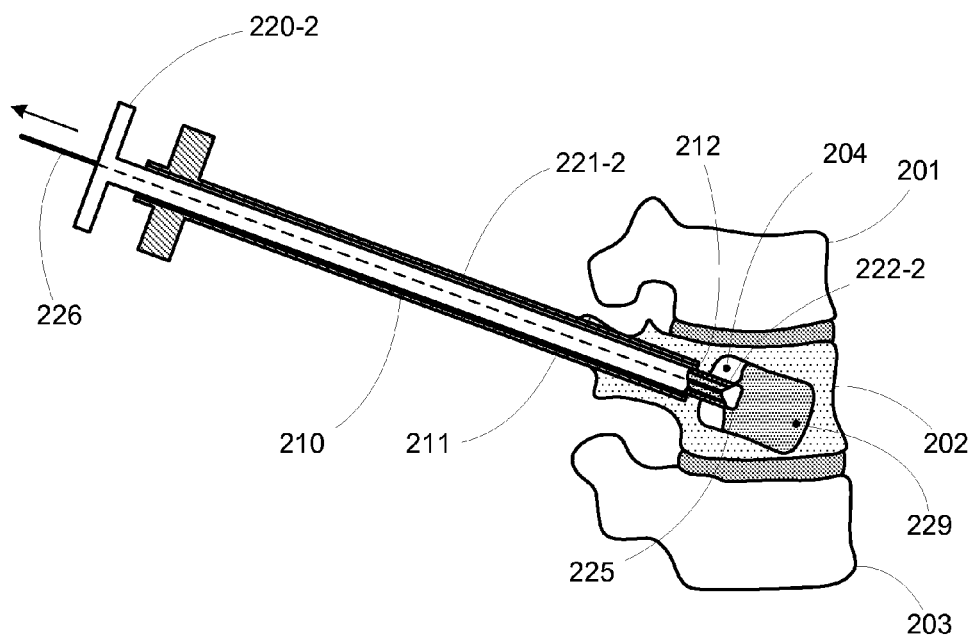

In one embodiment, nozzle 220-2 can include a valve at distal tip 222-2, as shown in FIGS. 5(A) and 5(B). A cable (or rod) 226 runs through the interior of nozzle 220-2 and is attached to a stopper 225. In FIG. 5(A), stopper 225 is extended beyond the distal tip 222-2 of nozzle 220-2. Because the diameter of cable 226 is less than the inner diameter of nozzle 220-2, the bone filler material 229 is able to flow around cable 226, past stopper 225, and into cavity 204. Once a desired amount of filling material 229 is dispensed, cable 226 can be moved proximally to pull stopper 225 against tip 222-2 of nozzle 220-2. This not only stops the flow of filler material 229, but also breaks any connection between the deposited filler material and the filler material remaining in nozzle 220-2.

In one embodiment, cable 226 can be spring loaded, such that stopper 225 is normally pulled against tip 222-2 of nozzle, but positive pressure from bone filler material 229 in nozzle 220-2 pushes stopper 225 away from tip 222-2. In another embodiment, cable 226 can be coupled to a reciprocating pumping mechanism for filler material 229, such that on every pumping stroke stopper 225 is moved away from tip 222-2, and on every non-pumping stroke (e.g., refill or suction), stopper 225 is seated against tip 222-2. Note that the tip valve formed by stopper 225 and cable 226 can be used in any nozzle for dispensing material into a target location, and need not be used with a nozzle that is part of a system that includes remote positioning control.

Figure 2I:
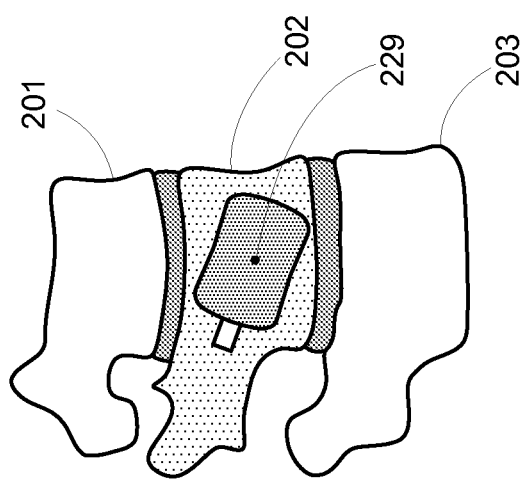

Once the filling operation is complete, nozzle 220-2 and cannula 210 are removed from vertebra 202 (and the patient's body) as shown in FIG. 2(I). Upon hardening, bone filler material 229 provides structural support for vertebra 202, thereby substantially restoring the structural integrity and proper musculoskeletal alignment of the spine. In this manner, the pain and attendant side effects of a vertebral compression fracture can be addressed by a minimally invasive kyphoplasty procedure.

Figure 3:
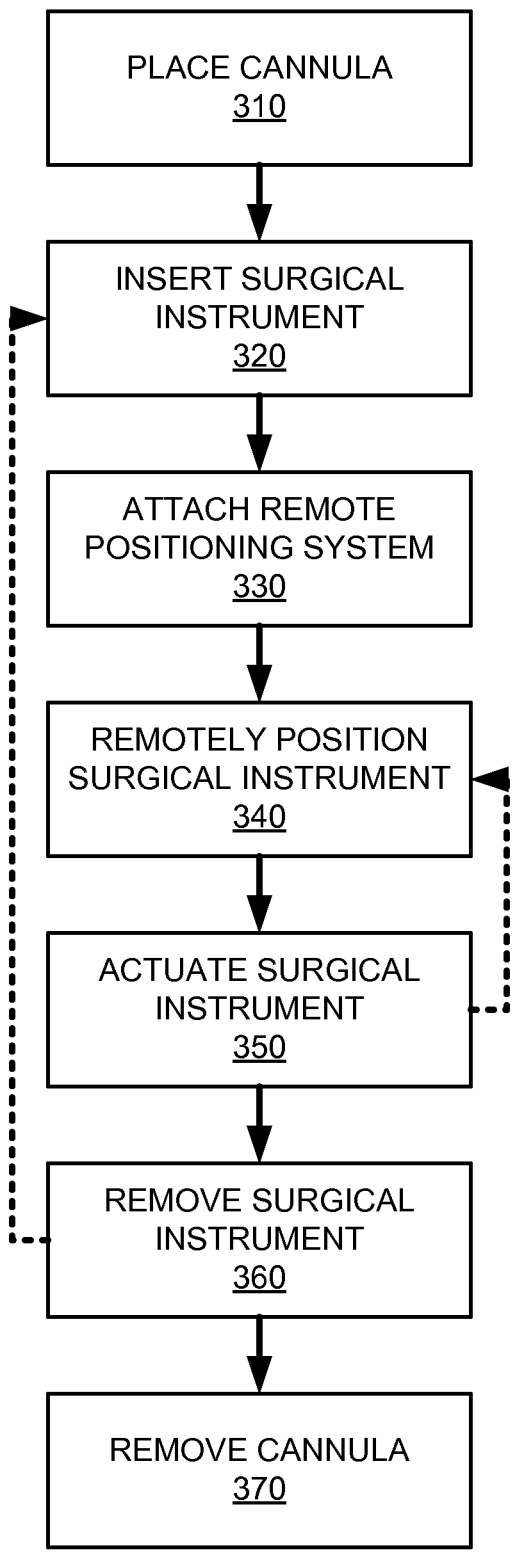
FIG. 3 shows a flow diagram of a percutaneous procedure in which a remote positioning system is used.

FIG. 3 shows a flow diagram of a process for performing a minimally invasive surgical procedure using the system of FIGS. 1 and 2(A)-2(I). In a PLACE CANNULA step 310, a cannula is placed in a patient such as described with respect to FIGS. 1 and 2(B), thereby creating an access path through which the surgical procedure can be performed. In various embodiments, step 310 can involve additional steps, such as inserting a guide needle to assist with placement of the cannula, and/or using a drill/obturator to extend the access path provided by the cannula.

Next, in an INSERT SURGICAL INSTRUMENT step 320, a surgical instrument is placed within the cannula. In various embodiments, the surgical instrument could be an inflatable bone tamp or a bone filler material delivery nozzle, as described above with respect to FIGS. 2(C) and 2(F), respectively. In various other embodiments, the surgical instrument could be any instrument for performing a surgical procedure through a cannula.

In an ATTACH REMOTE POSITIONING SYSTEM step 330, a positioning mechanism is attached to the cannula and the surgical instrument, such as described with respect to FIGS. 1, 2(C) and 2(F). Note that in some embodiments, the positioning mechanism can be pre-attached to the cannula and/or surgical instrument, in which case step 330 can be eliminated. Then, in a REMOTELY POSITION SURGICAL INSTRUMENT step 340, a remote position controller such as described with respect to FIGS. 1, 2(C), 2(F), and 2(G) is used to extend the surgical instrument out the distal end of the cannula to a desired location.

In an ACTUATE SURGICAL INSTRUMENT step 350, the surgical instrument is used to perform the surgical procedure (e.g., cavity creation within cancellous bone or bone filler material delivery, as described in FIGS. 2(D) and 2(F)-2(H), respectively). Note that in various embodiments, steps 340 and 350 can be performed simultaneously, or multiple times (as indicated by the dotted line arrow).

The surgical instrument and related apparatus (e.g., positioning system, actuating system) are then removed from the cannula in a REMOVE SURGICAL INSTRUMENT step 360. Optionally, a new surgical instrument can then be inserted into the cannula to perform another portion of the surgical procedure, as indicated by the dotted arrow. Finally, the cannula is removed from the patient in a REMOVE CANNULA step 370 to complete the surgical procedure.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain steps may be performed concurrently in a parallel process when possible, as well as performed sequentially as described above. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

The invention claimed is:

1. A system comprising:
a cannula extending along a longitudinal axis and comprising a lumen;
a surgical instrument coaxial with the cannula, the surgical instrument being sized to perform a surgical procedure through the lumen;
a positioning mechanism directly coupled to the cannula and the surgical instrument for moving the surgical instrument relative to the cannula, the positioning mechanism comprising a fixed element directly coupled to the cannula and an articulating element directly coupled to the surgical instrument such that the surgical instrument extends perpendicular to the articulating element, the fixed element comprising a first arm extending transverse to the axis and a second arm coupled to the first arm extending parallel to the axis, the articulating element being configured for axial translation along the second arm; and
a remote position controller for providing a control signal to the positioning mechanism, the positioning mechanism moving the surgical instrument relative to the cannula in response to the control signal.

2. The system of claim 1, wherein the remote position controller comprises:
a jacketed cable comprising an outer jacket and a flexible cable slidably disposed within the outer jacket; and
an adjustment mechanism for moving the cable relative to the outer jacket,
wherein the outer jacket is coupled to one of the fixed element and the articulating element, and
wherein the flexible cable is coupled to an other one of the fixed element and the articulating element.

3. The system of claim 2, wherein the adjustment mechanism comprises a lever rotatably attached to a housing of the remote position controller,
wherein the flexible cable is coupled to the lever, and
wherein the outer jacket is coupled to the housing of the remote position controller.

4. The system of claim 2, wherein the adjustment mechanism comprises:
a dial rotatably attached to a housing of the remote position controller; and a spool attached to the dial, wherein the outer jacket is coupled to the housing of the remote position controller, wherein the flexible cable is coupled to the spool, wherein turning the dial in a first direction rotates the spool to wind the flexible cable around the spool, and wherein turning the dial in a second direction rotates the spool to unwind the flexible cable from the spool.

5. The system of claim 4, wherein at least one of the dial and the spool comprises a plurality of engagement features, the system further comprising a latch, wherein the latch is selectably engageable with the plurality of engagement features to prevent rotation of the spool.

6. The system of claim 2, wherein the adjustment mechanism comprises a threaded element threadably mated with a housing of the remote position controller, wherein the outer jacket is coupled to the housing of the remote position controller, wherein the flexible cable is coupled to the threaded element, wherein rotating the threaded element with respect to the housing of the remote position controller moves the flexible cable relative to the outer jacket.

7. The system of claim 1, wherein the positioning mechanism further comprises a biasing element to bias the fixed element and the articulating element towards a default spacing.

8. The system of claim 1, wherein the remote position controller is adapted to cause the positioning mechanism to place the surgical instrument at one of a plurality of discrete positions relative to the cannula.

9. The system of claim 1, wherein the surgical instrument comprises a shaft and a cavity creation element at a distal end of the shaft for creating a cavity in cancellous bone.

10. The system of claim 1, wherein the surgical instrument comprises a nozzle for delivering bone filler material.

11. The system of claim 6, a fixed element coupled to the cannula and an articulating element coupled to the nozzle, the system further comprising:

a chamber of bone filler material coupled to the nozzle;

a hydraulic pump; and a first hydraulic line coupled to the chamber to cause bone filler material to flow into the nozzle, a second hydraulic line coupled to the positioning mechanism to cause the articulating element to move relative to the fixed element.

12. A method for performing a surgical procedure, the method comprising: providing a system comprising:

a cannula extending along a longitudinal axis and comprising a lumen that defines an access path to a target surgical location, a surgical instrument coaxial with the cannula, the surgical instrument being sized to perform a surgical procedure through the lumen, a positioning mechanism directly coupled to the cannula and the surgical instrument for moving the surgical instrument relative to the cannula, the positioning mechanism comprising a fixed element directly coupled to the cannula and an articulating element directly coupled to the surgical instrument such that the surgical instrument extends perpendicular to the articulating element, the fixed element comprising a first arm extending transverse to the axis and a second arm coupled to the first arm extending parallel to the axis, the articulating element being configured for axial translation along the second arm, and a remote position controller for providing a control signal to the positioning mechanism, the positioning mechanism moving the surgical instrument relative to the cannula in response to the control signal;

remotely controlling the positioning mechanism to adjust a position of the surgical instrument relative to the cannula.

13. The method of claim 12, wherein remotely controlling the positioning mechanism comprises:

providing a jacketed cable comprising a flexible cable slidably disposed in an outer jacket, a distal end of the outer jacket being coupled to at least one of the fixed element and the articulating element, and a distal end of the flexible cable being coupled to an other one of the fixed element and the articulating element; and applying a force to a proximal end of the flexible cable to move the flexible cable relative to the outer jacket.

14. The method of claim 12, wherein the surgical instrument comprises a nozzle, and wherein the method further comprises delivering bone filler material into a bone.

15. The method of claim 14, wherein remotely controlling the position of the surgical instrument relative to the cannula comprises moving a distal tip of the nozzle towards a distal tip of the cannula, and wherein delivering the bone filler material into the bone is performed concurrently with moving the distal tip of the nozzle towards the distal tip of the cannula.

16. The method of claim 14, wherein the target surgical location comprises a preformed cavity in cancellous bone within a vertebral body, wherein remotely controlling the position of the surgical instrument relative to the cannula comprises positioning a distal tip of the nozzle at a central location in the preformed cavity, and wherein delivering the bone filler material to the bone comprises substantially filling the preformed cavity with bone filler material without moving the distal tip of the nozzle.

17. The method of claim 12, wherein the target surgical location comprises a vertebral body, wherein the surgical instrument comprises a shaft and a cavity creation element at a distal end of the shaft, and wherein remotely controlling the positioning mechanism to adjust a position of the surgical instrument relative to the cannula comprises moving the cavity creation element within the vertebral body to manipulate a region of cancellous bone within the vertebral body.

18. The system of claim 1, wherein the remote position controller is coupled to the second arm via a cable.

19. The system of claim 1, wherein the articulating element is coupled to the second arm via a sliding interface.

20. The system of claim 1, wherein the articulating element is fixed to an outer surface of the surgical instrument.

* * * * *

UNITED STATES PATENT AND TRADEMARK OFFICE
CERTIFICATE OF CORRECTION

| | | |
|---|---|---|
| PATENT NO. | : 8,617,053 B2 | Page 1 of 1 |
| APPLICATION NO. | : 12/430044 | |
| DATED | : December 31, 2013 | |
| INVENTOR(S) | : Donovan et al. | |

It is certified that error appears in the above-identified patent and that said Letters Patent is hereby corrected as shown below:

In the Claims:

In Column 14, Line 10, in Claim 12, delete "signal;" and insert -- signal; and --, therefor.

Signed and Sealed this
Nineteenth Day of August, 2014

Michelle K. Lee
*Deputy Director of the United States Patent and Trademark Office*